Nov. 7, 1961 C. W. GREGORY Plant Pat. 2,104
ROSE PLANT
Filed Dec. 14, 1960
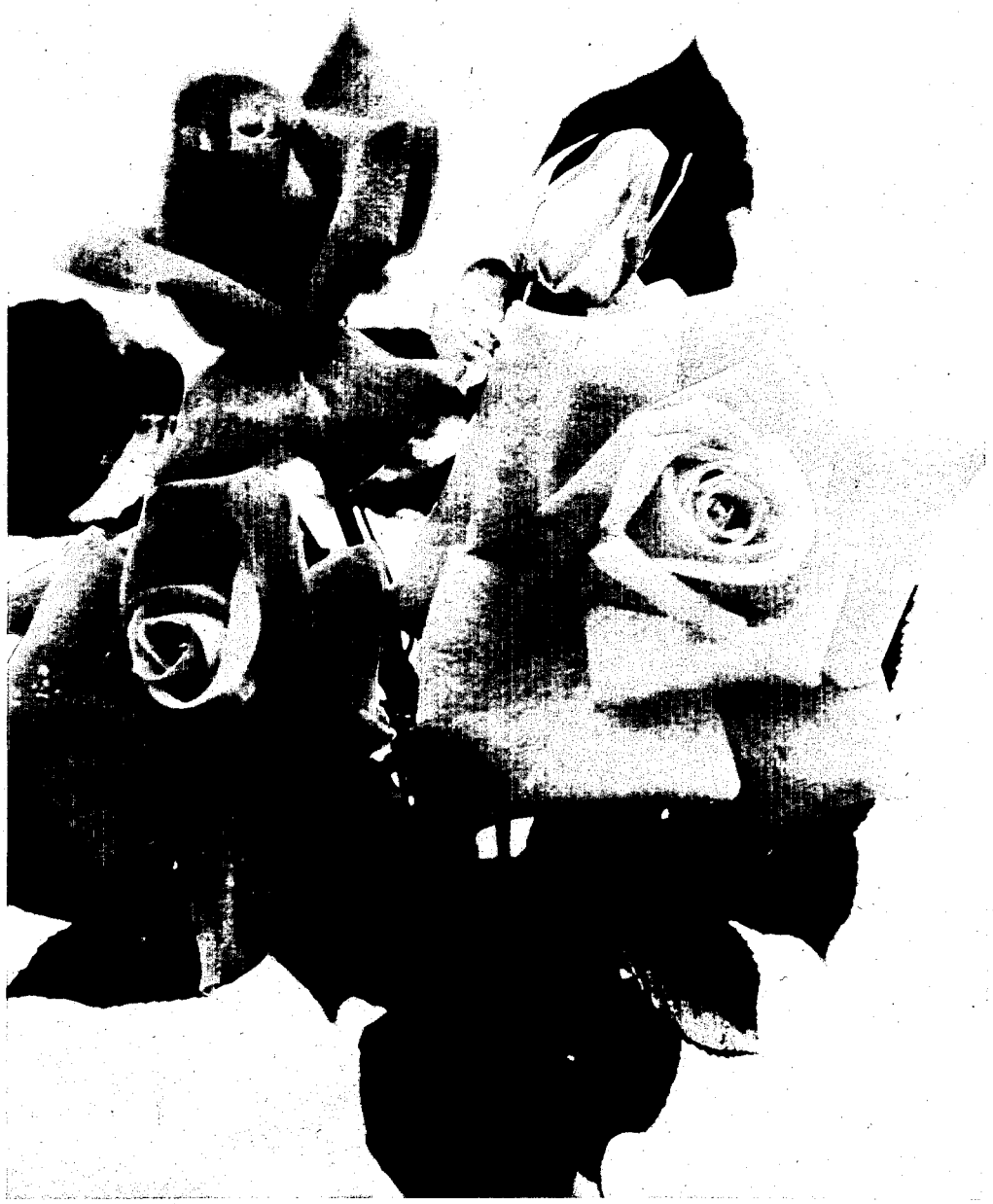
INVENTOR
Charles W. Gregory
BY Robb & Robb
ATTORNEYS United States Patent Office Plant Pat. 2,104
Patented Nov. 7, 1961

2,104
ROSE PLANT

Charles W. Gregory, Chilwell, Nottingham, England, assignor, by mesne assignments, to Ilgenfritz Nurseries, Inc., Monroe, Mich., a corporation of Michigan Filed Dec. 14, 1960, Ser. No. 75,897
1 Claim. (Cl. 47—61)

The present invention relates to a new and distinct variety of rose plant of the hybrid tea class, which was originated by me by crossing two unnamed and unpatented seedlings of unknown origin, but which I believe were respectively the variety "Independence" (U.S. Plant Patent No, 1,036) and the variety "Eden Rose" (U.S. Plant Patent No. 1,149).

As the result of this breeding, I have produced a new rose variety which is endowed with the following unique combination of outstanding characteristics which distinguish the same from its parents, as well as from all other varieties of which I am aware:

(1) A vigorous and healthy habit of growth;
(2) Perfectly shaped blooms;
(3) A distinctive and attractive Cherry general color tonality of the flowers; and
(4) A very strong tea fragrance.

Asexual reproduction of my new variety by budding, as performed by me at Chilwell, Nottingham, England, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with the Horticultural Colour Chart issued by the British Colour Council in collaboration with the Royal Horticultural Society, except where general color terms of ordinary dictionary significance are obvious:

Type: Hardy; bush; outdoor; seedling; for cut flowers and for garden decoration.
Class: Hybrid tea.
Breeding: Seedling.
*Seed parent.*—An unidentified seedling, but believed to be the variety named "Independence" (known in Germany as "Kordes' Sondermeldung").
*Pollen parent.*—An unidentified seedling, but believed to be the variety known as "Eden Rose."
Propagation: Holds its distinguishing characteristics through succeeding propagations by budding.

*Flower*

Locality where grown and observed: Chilwell, Nottingham, England.
Continuity: Continuous.
Fragrance: Strong. Nature—tea.
Flowers borne: Usually 2 or 3, but sometimes more, to stem; in regular clusters; on long stems.
Quantity of bloom: Abundant, outdoors.
Bud:
*Peduncle.*—Medium length; heavy; erect; stiff; medium smoothness; with numerous brown prickles. Color—green-bronze.
*Before calyx breaks.*—Size—large. Form—long; pointed; without foliaceous appendages on the surface of the bud; with entire foliaceous parts extending beyond the tip of the bud equal to ½ or more of its length. Color—Lettuce Green, Plate 861/3.
*As calyx breaks.*—Color—medium green.
*As first pedal opens.*—Size—large. Form—pointed. Color: outside—Cherry, Plate 722/3; inside—Cherry, Plate 722.
*Opening.*—Opens up well under all conditions.
Bloom:
*Size (when fully open).*—Large; from 5 inches to 6 inches.
*Petalage.*—Very double; from 28 to 33 petals; arranged regularly.
*Form.*—High-centered at first, and remaining high-centered; both inside and outside petals have strong tendency to reflex, which becomes more pronounced as blooms open, and the outside petals become very tightly rolled outwards.
Petals:
*Texture.*—Thick; leathery.
*Appearance.*—Inside—Satiny. Outside—shiny.
*Shape.*—Outside—round, with one notch. Intermediate—round. Inside—round.

This description of a newly opened flower was made from a rose grown outdoors during the month of August at Chilwell, Nottingham, England:

*Color.*—Outer petal: outside surface—Cherry, Plate 722/3; inside surface—Cherry, Plate 722. Intermediate petal: outside surface—Cherry, Plate 722/3; inside surface—Cherry, Plate 722. Inner petal: outside surface—Cherry, Plate 722/3; inside surface—Cherry, Plate 722.

This description was made from a rose that was open for 3 days outdoors during the month of August at Chilwell, Nottingham, England:

*Color.*—Outer petal: outside surface—Cherry, Plate 722/3; inside surface—Cherry, Plate 722. Intermediate petal: outside surface—Cherry, Plate 722/3; inside surface—Cherry, Plate 722. Inner petal: outside surface—Cherry, Plate 722/3; inside surface—Cherry, Plate 722.
*General color effect.*—Newly opened flower—Cherry. 3-days open—Cherry.
*Behavior.*—Drop off cleanly.
*Flower longevity.*—On bush in garden—5 days in August. Cut flowers grown outdoors and kept at living room temperatures—5 days in August. Cut flowers grown in greenhouse and kept at living room temperatures—4 days in August.

*Reproductive organs*

Stamens: Many; arranged regularly about pistils. Color—gold.
Filaments: Long; most with anthers. Color—reddish.
Anthers: Large. Color—yellow.
Pollen: Abundant. Color—yellow.
Pistils: Many.
Styles: Even; medium length; medium caliper; loosely bunched.
Stigma: Color—yellow.
Ovaries: All enclosed in calyx.
Hips: Ovoid; smooth; walls thick and fleshy. Color—green.
Sepals: Permanent; long; spear-shaped. Color—light green.
Seeds: Many; medium size.

*Plant*

Foliage:
*Leaves*—Compound of 5–7 leaflets; very abundant; medium large; leathery; glossy.

*Leaflets.*—Shape—ovoid, with apex acute. Base—round. Margin—serrate.

*Color (mature).*—Upper side—Ivy Green, Plate 1060. Under side—Leek Green, Plate 000858, with inconsistent purple shading.

*Rachis (the supporting stem of the compound leaf).*—Medium. Upper side—smooth. Under side—moderately thorny. Color—light brown.

*Stipules.*—Medium length; medium width; with points turning out at an angle of more or less 45°. Color—light red.

*Disease resistance.*—Good resistance to both mildew and blackspot, as determined from comparison with other varieties grown under comparable cultural conditions at Chilwell, Nottingham, England.

Growth:

*Habit.*—Bushy; much-branched.

*Growth.*—Free; vigorous.

*Canes.*—Heavy.

*Main stems.* — Color — brown. Thorns — many; hooked downward; with long, broad, round base; color—Garnet Brown, Plate 00918. Prickles—none. Hairs—none.

*Branches.*—Color—green-bronze. Thorns — many, hooked downward; with long, broad, round base. Prickles—none. Hairs—none.

*New shoots.*—Color—bright bronze. Thorns—many; long; hooked downward; with long, broad, round base. Prickles—none. Hairs—none.

I claim:

A new and distinct variety of rose plant of the hybrid tea class, substantially as herein shown and described, characterized particularly as to novelty by the unique combination of a vigorous and healthy habit of growth, perfectly shaped blooms, a distinctive and attractive Cherry general color tonality of the flowers, and a very strong tea fragrance of the flowers.

No references cited.